US010414719B2

(12) United States Patent
Ebert et al.

(10) Patent No.: US 10,414,719 B2
(45) Date of Patent: *Sep. 17, 2019

(54) ETHERAMINES BASED ON DIALCOHOLS

(71) Applicant: BASF SE, Ludwigshafen (DE)

(72) Inventors: Sophia Ebert, Mannheim (DE); Björn Ludolph, Ludwigshafen (DE); Christof W. Wigbers, Lich (DE); Christian Eidamshaus, Wiesloch (DE); Dieter Boeckh, Limburgerhof (DE); Frank Huelskoetter, Bad Dürkheim (DE); Brian J. Loughnane, Sharonville, OH (US); Amy Eichstadt Waun, Loveland, OH (US); Kevin Christmas, Mason, OH (US); Darren Rees, Newcastle upon Tyne (GB); Stefano Scialla, Rome (IT)

(73) Assignee: BASF SE (DE)

( * ) Notice: Subject to any disclaimer, the term of this patent is extended or adjusted under 35 U.S.C. 154(b) by 153 days.

This patent is subject to a terminal disclaimer.

(21) Appl. No.: 15/129,169

(22) PCT Filed: Mar. 11, 2015

(86) PCT No.: PCT/EP2015/055053
§ 371 (c)(1),
(2) Date: Sep. 26, 2016

(87) PCT Pub. No.: WO2015/144436
PCT Pub. Date: Oct. 1, 2015

(65) Prior Publication Data
US 2018/0179145 A1 Jun. 28, 2018

Related U.S. Application Data

(60) Provisional application No. 61/993,317, filed on May 15, 2014.

(30) Foreign Application Priority Data

Mar. 27, 2014 (EP) .................................. 14162043

(51) Int. Cl.
C07C 217/08 (2006.01)
B29C 35/00 (2006.01)
B29C 33/56 (2006.01)
C07C 213/02 (2006.01)
C08G 18/32 (2006.01)
C07C 213/04 (2006.01)
A61K 8/45 (2006.01)
A61Q 5/02 (2006.01)
A61K 8/86 (2006.01)
A61Q 19/10 (2006.01)
C11D 1/44 (2006.01)
C11D 3/37 (2006.01)
C11D 3/30 (2006.01)

(52) U.S. Cl.
CPC .............. *C07C 217/08* (2013.01); *A61K 8/45* (2013.01); *A61K 8/86* (2013.01); *A61Q 5/02* (2013.01); *A61Q 19/10* (2013.01); *B29C 33/56* (2013.01); *B29C 35/00* (2013.01); *C07C 213/02* (2013.01); *C07C 213/04* (2013.01); *C08G 18/3228* (2013.01); *C11D 1/44* (2013.01); *C11D 3/30* (2013.01); *C11D 3/3707* (2013.01)

(58) Field of Classification Search
CPC ......... C11D 3/30; C11D 3/3723; B29C 33/56; B29C 35/00
USPC ......... 510/475, 499; 106/38.2, 38.22, 287.23
See application file for complete search history.

(56) References Cited

U.S. PATENT DOCUMENTS

| | | | |
|---|---|---|---|
| 4,820,436 A | 4/1989 | Andree et al. | |
| 5,530,127 A | 6/1996 | Reif et al. | |
| 8,318,982 B2 | 11/2012 | Kubanek et al. | |
| 8,487,135 B2 | 7/2013 | Kubanek et al. | |
| 8,530,570 B2 | 9/2013 | Mijolovic et al. | |
| 9,068,147 B2 | 6/2015 | Dobrawa et al. | |
| 9,193,939 B2 | 11/2015 | Hulskotter et al. | |
| 9,974,985 B2 * | 5/2018 | Ebert | A61Q 19/10 |
| 2005/0234216 A1 | 10/2005 | Klein et al. | |
| 2011/0040030 A1 | 2/2011 | Mijolovic et al. | |
| 2011/0130514 A1 | 6/2011 | Mijolovic et al. | |
| 2011/0144259 A1 | 6/2011 | Mijolovic et al. | |
| 2011/0178239 A1 | 7/2011 | Mijolovic et al. | |
| 2013/0243676 A1 | 9/2013 | Siskin et al. | |
| 2013/0324451 A1 | 12/2013 | Dobrawa et al. | |
| 2015/0057212 A1 | 2/2015 | Hulskotter et al. | |
| 2015/0057213 A1 | 2/2015 | Hulskotter et al. | |

(Continued)

FOREIGN PATENT DOCUMENTS

| | | |
|---|---|---|
| EP | 0696572 A1 | 2/1996 |
| JP | 2005-537350 A | 12/2005 |

(Continued)

OTHER PUBLICATIONS

International Preliminary Report on Patentability for Application No. PCT/EP2015/055053, dated Sep. 27, 2016.

(Continued)

*Primary Examiner* — Gregory R Delcotto
(74) *Attorney, Agent, or Firm* — Drinker Biddle & Reath LLP

(57) ABSTRACT

This invention relates to etheramines based on dialcohols, wherein the etheramines comprise at least three linear or branched $C_4$-alkylene groups and a process for the manufacture of these etheramines.

19 Claims, No Drawings

(56) References Cited

U.S. PATENT DOCUMENTS

| | | |
|---|---|---|
| 2015/0210952 A1 | 7/2015 | Desantis et al. |
| 2015/0210956 A1 | 7/2015 | Desantis et al. |
| 2015/0329476 A1 | 11/2015 | Ebert et al. |
| 2016/0052867 A1 | 2/2016 | Ebert et al. |
| 2016/0251304 A1 | 9/2016 | Ebert et al. |

FOREIGN PATENT DOCUMENTS

| | | | |
|---|---|---|---|
| JP | 2013-181000 A | | 9/2013 |
| WO | WO-198607603 A1 | | 12/1986 |
| WO | WO-199003423 A1 | | 4/1990 |
| WO | WO00/63334 | * | 10/2000 |
| WO | WO01/76729 | * | 10/2001 |
| WO | WO-0176729 A2 | | 10/2001 |
| WO | WO-2004020506 A2 | | 3/2004 |
| WO | WO-2009065738 A2 | | 5/2009 |
| WO | WO-2009-138387 A1 | | 11/2009 |
| WO | WO-2009153193 A1 | | 12/2009 |
| WO | WO-2010010075 A1 | | 1/2010 |
| WO | WO-2010026030 A1 | | 3/2010 |
| WO | WO-2010026066 A1 | | 3/2010 |
| WO | WO-2011067199 A1 | | 6/2011 |
| WO | WO-2011067200 A1 | | 6/2011 |
| WO | WO-2011087793 A1 | | 7/2011 |

OTHER PUBLICATIONS

International Search Report for Application No. PCT/EP2015/055053, dated Sep. 27, 2016.

"The Jeffamine Polyetheramines", *Huntsman*, 6 pages (2007).

"JEFFAMINE D-230 Polyetheramine", Technical Bulletin, Hunstman.

International Search Report for PCT/EP2015/055053 dated May 15, 2015.

\* cited by examiner

ETHERAMINES BASED ON DIALCOHOLS

CROSS-REFERENCE TO RELATED APPLICATIONS

This application is a national stage application (under 35 U.S.C. § 371) of PCT/EP2015/055053, filed Mar. 11, 2015, which claims benefit of European Application No. 14162043.5, filed Mar. 27, 2014, and U.S. Application No. 61/993,317, filed May 15, 2014, all of which are incorporated herein by reference in their entirety.

This invention relates to etheramines based on dialcohols, wherein the etheramines comprise at least three linear or branched $C_4$-alkylene groups and a process for the manufacture of these etheramines.

Due to the increasing popularity of easy-care fabrics made of synthetic fibers as well as the ever increasing energy costs and growing ecological concerns of detergent users, the once popular hot water wash has now taken a back seat to washing fabrics in cold water. Many commercially available laundry detergents are even advertised as being suitable for washing fabrics at 40° C. or 30° C. or even at room temperature. To achieve satisfactory washing results at such low temperatures, results comparable to those obtained with hot water washes, the demands on low-temperature detergents are especially high.

It is known to include certain additives in detergent compositions to enhance the detergent power of conventional surfactants so as to improve the removal of grease stains at temperatures of 60° C. and below.

WO 1986/07603 discloses that detergent composition comprising an aliphatic amine compound, in addition to at least one synthetic anionic and/or nonionic surfactant, are known and have led to improved cleaning results even at low wash temperatures. These compounds are said to contribute to the improvement of the washing performance of the detergent at lower temperatures. Also, the use of linear, alkyl-modified (secondary) alkoxypropylamines in laundry detergents to improve cleaning at low temperatures is known (WO 1990/03423). These known laundry detergents, however, are unable to achieve satisfactory cleaning when laundry is washed at cold temperatures.

Furthermore, the use of linear, primary polyoxyalkyleneamines (e.g., Jeffamine® D-230) to stabilize fragrances in laundry detergents and provide longer lasting scent is also known (WO2009/065738). Also, the use of high-moleculer-weight (molecular weight of at least about 1000), branched, trifunctional, primary amines (e.g., Jeffamine® T-5000 polyetheramine) to suppress suds in liquid detergents is known (WO 2001/76729).

Additionally, WO 2011/087793 reads on etheramine mixtures comprising at least 10 wt % of an alkoxylated monoether amine based on polyhydric alcohols containing 2 to 4 hydroxyl groups as the starting compound. A process for the manufacture of these etheramine mixtures is also disclosed. These products find an application as a curing agent or as a raw material in the synthesis of polymers. WO 2004/020506 discloses polyamines based on polyhydric alcohols alkoxylated with butylene oxide and processes for preparing cured epoxy (poly-(etheralkanolamine)) resin or polyurea with these polyamines.

There is a continuous need for cleaning compositions that remove grease stains from fabrics and other soiled materials, as grease stains are challenging stains to remove. Conventional cleaning compositions directed to grease removal frequently utilize various amine compounds which tend to show strong negative impacts on whiteness. As a consequence there is still a continual need for improved amine compositions which provide improved grease removal from fabrics and other soiled materials and at the same time do not negatively impact the clay cleaning.

It was an object of the present invention to provide compounds which would improve the washing performance of detergents at low temperatures, i.e. at temperatures as low as 30° C. or even lower.

This goal was achieved with an etheramine of formula (I)

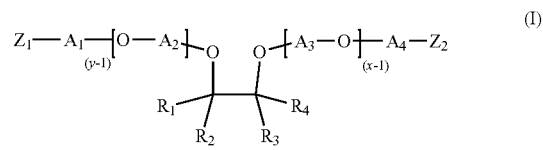

or formula (II)

$$Z_3 \quad O\!\!-\!\!\left[A_2\!-\!O\right]_{(x\text{-}1)}\!\!\left[A_3\!-\!O\right]_{(y)}\!\!-\!\!A_1\!-\!Z_4 \quad (II)$$
$$R_1 \quad R_4$$
$$R_2 \quad R_3$$

or a mixture of etheramines of formula (I) and formula (II);

wherein $R_1$, $R_2$, $R_3$ and $R_4$ are independently selected from the group consisting of H, a methyl group and an ethyl group;

wherein $A_1$, $A_2$, $A_3$ and $A_4$ are independently selected from the group consisting of linear alkylenes having 2 to 18 carbon atoms and branched alkylenes having 2 to 18 carbon atoms; wherein at least three selected from the group consisting of $A_1$, $A_2$, $A_3$ and $A_4$ are linear or branched butylene;

wherein the sum of x+y is in the range of 3 to 100 and x≥1 and y≥1;

wherein $Z_1$-$Z_4$ are independently selected from OH, $NH_2$, NHR' or NR'R", wherein at least one of $Z_1$-$Z_2$ and at least one of $Z_3$-$Z_4$ is $NH_2$, NHR' or NR'R", wherein R' and R" are independently selected from alkylenes having 2 to 6 carbon atoms.

Preferably, the sum of x and y is in the range of 3 to 20, preferably in the range of 3 to 10, more preferably in the range of 3 to 8, more preferably in the range of 3 to 6 and even more preferably in the range of 3 to 4.

In a preferred embodiment, the mixture of etheramines of formula (I) and formula (II) comprises at least 80% by weight, based on the total weight of the etheramine mixture, of the amine of Formula (I) and/or (II), preferably at least 90% by weight.

In another preferred embodiment, $A_1$, $A_2$, $A_3$ and $A_4$ are independently selected from the group consisting of ethylene, propylene, or butylene, preferably $A_1$, $A_2$, $A_3$ and A are linear or branched butylene.

In a preferred embodiment, $R_1$ is a methyl group and $R_2$, $R_3$ and $R_4$ are H. In another preferred embodiment, $R_1$ is an ethyl group and $R_2$, $R_3$ and $R_4$ are H. In a further preferred embodiment, $R_1$ and $R_3$ are methyl groups and $R_2$ and $R_4$ are H.

In a preferred embodiment, $Z_1$-$Z_4$ are $NH_2$.

The etheramine of formula (I) or formula (II) has a weight average molecular weight of about 250 to about 700 grams/ mole, preferably, of about 270 to about 700 grams/mole, even more preferably of about 370 to about 570 grams/mole.

In a preferred embodiment, the degree of amination in the etheramines of the present invention is between 50 to 100%, preferably from 60 to 100% and most preferably from 70-100%. The degree of amination is calculated from the total amine value (AZ) divided by sum of the total acetylables value (AC) and tertiary amine value (tert. AZ) multiplied by 100: (Total AZ: (AC+tert. AZ)×100).

The total amine value (AZ) is determined according to DIN 16945, March 1989. The total acetylables value (AC) is determined according to DIN 53240, December 1971. The secondary and tertiary amines are determined according to ASTM D2074-07, July 2007.

The hydroxyl value is calculated from (total acetylables value+tertiary amine value)−total amine value.

The present invention further relates to a composition comprising an etheramine of formula (I) and/or formula (II) and an etheramine of formula (VI)

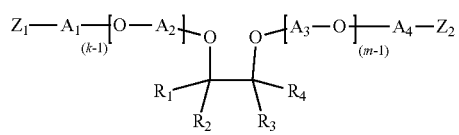

(VI)

and/or an etheramine of formula (VII)

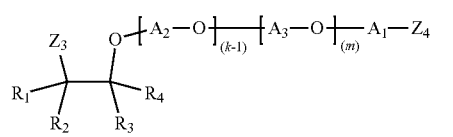

(VII)

wherein $R_1$, $R_2$, $R_3$ and $R_4$ are independently selected from the group consisting of H, a methyl group and an ethyl group;

wherein $A_1$, $A_2$, $A_3$ and $A_4$ are independently selected from the group consisting of linear alkylenes having 2 to 18 carbon atoms and branched alkylenes having 2 to 18 carbon atoms;

wherein at least one of $A_1$, $A_2$, $A_3$ and $A_4$ is linear or branched butylene;

wherein the sum of k+m is below 3 and wherein k≥1 and m≥1;

wherein $Z_1$-$Z_4$ are independently selected from OH, $NH_2$, NHR' or NR'R", wherein at least one of $Z_1$-$Z_2$ and at least one of $Z_3$-$Z_4$ is $NH_2$, NHR' or NR'R", wherein R' and R" are independently selected from alkylenes having 2 to 6 carbon atoms.

In a preferred embodiment, $Z_1$-$Z_4$ are $NH_2$.

Preferably, this composition comprises at least 80% by weight, preferably at least 90% by weight of etheramines of formula (I) and/or formula (II) and about 0 to 20% by weight, preferably about 0 to 10% by weight of etheramines of formula (VI) and/or formula (VII).

In another preferred embodiment, the inventive etheramine or etheramine composition is further reacted with an acid. The acid may be selected from the group consisting of citric acid, lactic acid, sulfuric acid, methanesulfonic acid, hydrogen chloride, phosphoric acid and mixtures thereof. In an alternative embodiment, the etheramines of the invention may, in protonated form, have a surfactant as a counter ion, as obtained from e.g. linear alkyl benzene sulphonic acid.

The etheramine as defined above is obtainable by a process comprising the following steps:

a) reacting of dialcohols of formula (III) with $C_2$-$C_{18}$ alkylene oxides, wherein the molar ratio of dialcohol to $C_2$-$C_{18}$ alkylene oxides is in the range of 1:3 to 1:10,

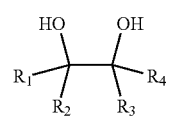

(III)

wherein $R_1$, $R_2$, $R_3$ and $R_4$ are independently selected from the group consisting of H, a methyl group or an ethyl group; and b) the amination of the alkoxylated dialcohols with ammonia.

In a preferred embodiment, an etheramine mixture is obtained comprising at least 90% by weight, based on the total weight of the etheramine mixture, of the etheramine according to Formula (I) and (II).

In a preferred embodiment the molar ratio of dialcohol to $C_2$-$C_{18}$ alkylene oxides is in the range of 1:3 to 1:8, preferably in the range of 1:3 to 1:6 and even more preferably in the range of 1:3 to 1:4.

Preferably the $C_2$-$C_{18}$ alkylene oxides are selected from the group consisting of ethylene oxide, propylene oxide, butylene oxide or a mixture thereof, even more preferably $C_2$-$C_{18}$ alkylene oxide is butylene oxide.

Preferably in the dialcohol of formula (III), $R_1$ is a methyl group and $R_2$, $R_3$ and $R_4$ are H. In another preferred embodiment, $R_1$ is an ethyl group and $R_2$, $R_3$ and $R_4$ are H. In a further preferred embodiment, $R_1$ and $R_3$ are methyl groups and $R_2$ and $R_4$ are H.

The dialcohol of formula (III) is preferably selected from the group consisting of 1,2-propanediol, 1,2-butanediol, 1,2-ethanediol, 3,4-hexanediol, 2,3-pentanediol.

In the following, step a): alkoxylation of the process is described in more detail:

Substituted dialcohols (formula (III)) are synthesized according WO 10/026030, WO 10/026066, WO 09/138387, WO 09/153193, WO 10/010075.

Suitable dialcohols (formula III) are for example: 1,2-propanediol, 1,2-butanediol, 1,2-ethanediol, 3,4-hexanediol, 2,3-pentanediol, etc.

Alkoxylated dialcohols are obtained by reaction of dialcohols (formula (III)) with alkylene oxides and can be effected according to general alkoxylation procedures known in the art.

The alkoxylated dialcohols may be prepared in a known manner by reaction of dialcohols with alkylene oxides. Suitable alkylene oxides are $C_2$-$C_{18}$ alkylene oxides like ethylene oxide, propylene oxide, butylene oxide, pentene oxide, hexene oxide, decene oxide, dodecene oxide etc. Preferred $C_2$-$C_{18}$ alkylene oxides are ethylene oxide, propylene oxide, butylene oxide or a mixture thereof.

The dialcohols are reacted with one single alkylene oxide or combinations of two or more different alkylene oxides. Using two or more different alkylene oxides, the resulting polymer can be obtained as a block-wise structure or a random structure.

The molar ratio of molar ratio of dialcohol to $C_2$-$C_{18}$ alkylene oxides at which the alkoxylation reaction is carried out lies in the range of 1:3 to 1:10, preferably in the range of 1:3 to 1:6, more preferably in the range of 1:3 to 1:8, even more preferably in the range of 1:3 to 1:4.

This reaction is performed generally in the presence of a catalyst in an aqueous solution at a reaction temperature from about 70'C to about 200'C and preferably from about 80° C. to about 160° C. This reaction may be affected at a pressure of up to about 10 bar, and in particular up to about 8 bar.

Examples of suitable catalysts are basic catalysts such as alkali metal and alkaline earth metal hydroxides such as sodium hydroxide, potassium hydroxide and calcium hydroxide, alkali metal alkoxides, in particular sodium and potassium $C_1$-$C_4$-alkoxides, such as sodium methoxide, sodium ethoxide and potassium tert-butoxide, alkali metal and alkaline earth metal hydrides such as sodium hydride and calcium hydride, and alkali metal carbonates such as sodium carbonate and potassium carbonate. Preference is given to alkali metal hydroxides, particular preference being given to potassium hydroxide and sodium hydroxide. Typical use amounts for the base are from 0.05 to 10% by weight, in particular from 0.1 to 2% by weight, based on the total amount of polyalkyleneimine and alkylene oxide.

Alkoxylation with x+y $C_2$-$C_{18}$ alkylene oxides leads to structures as drawn in formula IV and/or formula V:

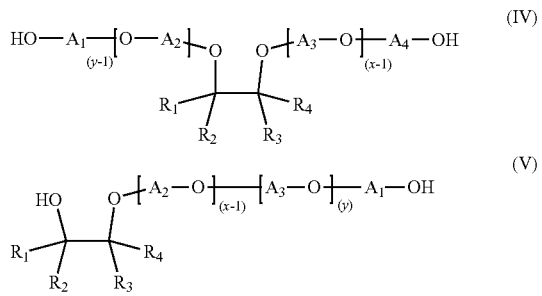

wherein $R_1$, $R_2$, $R_3$ and $R_4$ are independently selected from the group consisting of H, a methyl group and an ethyl group;

wherein $A_1$, $A_2$, $A_3$ and $A_4$ are independently selected from the group consisting of linear alkylenes having 2 to 18 carbon atoms and branched alkylenes having 2 to 18 carbon atoms;

wherein at least three selected from the group consisting of $A_1$, $A_2$, $A_3$ and $A_4$ are linear or branched butylene;

wherein the sum of x+y is in the range of 3 to 100 and x≥1 and y≥1.

In the following, step b): amination of the process is described in more detail:

Amination of the alkoxylated dialcohol leads to new structures with formula (I):

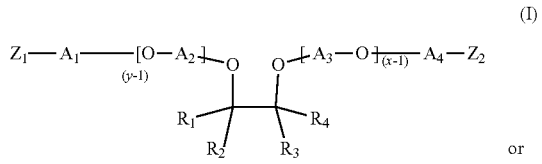

or

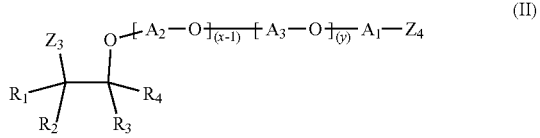

or a mixture of etheramines of formula (I) and formula (II);

wherein $R_1$, $R_2$, $R_3$ and $R_4$ are independently selected from the group consisting of H, a methyl group and an ethyl group;

wherein $A_1$, $A_2$, $A_3$ and $A_4$ are independently selected from the group consisting of linear alkylenes having 2 to 18 carbon atoms and branched alkylenes having 2 to 18 carbon atoms; wherein at least three selected from the group consisting of $A_1$, $A_2$, $A_3$ and $A_4$ are linear or branched butylene;

wherein the sum of x+y is in the range of 3 to 100 and x≥1 and y≥1;

wherein $Z_1$-$Z_4$ are independently selected from OH, $NH_2$, NHR' or NR'R", wherein at least one of $Z_1$-$Z_2$ and at least one of $Z_3$-$Z_4$ is $NH_2$, NHR' or NR'R", wherein R' and R" are independently selected from alkylenes having 2 to 6 carbon atoms.

Etheramines according to formula (I) and/or (II) are obtained by reductive amination of the alkoxylated dialcohol mixture (formula IV and V) with ammonia in presence of hydrogen and a catalyst containing nickel. Suitable catalysts are described in WO 11/067199 A1 and in WO 11/067200 A1, and in EP 0 696 572 B1. Preferred catalysts are supported copper-, nickel- and cobalt-containing catalysts, wherein the catalytically active material of the catalysts, before the reduction thereof with hydrogen, comprises oxygen compounds of aluminium, of copper, of nickel and of cobalt, and in the range from 0.2 to 5.0% by weight of oxygen compounds of tin, calculated as SnO. Other preferred catalysts are supported copper-, nickel- and cobalt-containing catalysts, wherein the catalytically active material of the catalysts, before the reduction thereof with hydrogen, comprises oxygen compounds of aluminium, of copper, of nickel, of cobalt and of tin, and in the range from 0.2 to 5.0% by weight of oxygen compounds of yttrium, of lanthanum, of cerium and/or of hafnium, each calculated as $Y_2O_3$, $La_2O_3$, $Ce_2O_3$ and $Hf_2O_3$ respectively. Another preferred catalyst is a zirconium, copper, nickel catalyst, wherein the catalytically active composition comprises from 20 to 85% by weight of oxygen-containing zirconium compounds, calculated as ZrO2, from 1 to 30% by weight of oxygen-containing compounds of copper, calculated as CuO, from 30 to 70% by weight of oxygen-containing compounds of nickel, calculated as NO, from 0.1 to 5% by weight of oxygen-containing compounds of aluminium and/or manganese, calculated as Al2O3 and MnO2 respectively.

For the reductive amination step supported as well as non-supported catalyst can be used. The supported catalyst e.g. Is obtained by deposition of the metallic components of the catalyst compositions onto support materials known to those skilled in the art, using techniques which are well-known in the art including without limitation, known forms of alumina, silica, charcoal, carbon, graphite, clays, mordenites; and molecular sieves, to provide supported catalysts as well. When the catalyst is supported, the support particles of the catalyst may have any geometric shape, for example the shape of spheres, tablets or cylinders in a regular or irregular version. The process can be carried out in a continuous or discontinuous mode, e.g. in an autoclave, tube reactor or fixed-bed reactor. The reactor design is also not narrowly critical. The feed thereto may be upflowing or downflowing, and design features in the reactor which optimize plug flow in the reactor may be employed.

In a preferred embodiment, the degree of amination in the process of the present invention is between 50 to 100%, preferably from 60 to 100% and most preferably from 70-100%.

The degree of amination is calculated from the total amine value (AZ) divided by sum of the total acetylables value (AC) and tertiary amine value (tert. AZ) multiplied by 100: (Total AZ: (AC+tert. AZ)×100).

The total amine value (AZ) is determined according to DIN 16945, March 1989. The total acetylables value (AC) is determined according to DIN 53240, December 1971. The secondary and tertiary amines are determined according to ASTM D2074-07, July 2007.

The hydroxyl value is calculated from (total acetylables value+tertiary amine value)−total amine value.

Etheramines of formula (VI) and (VII) can be obtained in a similar way as the etheramines of formula (I) and (II).

In another preferred embodiment, the etheramines of the invention can also be further reacted with an acid. The acid may be selected from the group consisting of citric acid, lactic acid, sulfuric acid, methanesulfonic acid, hydrogen chloride, phosphoric acid, formic acid, acetic acid, propionic acid, valeric acid, oxalic acid, succinic acid, adipic acid, sebacic acid, glutaric acid, glucaric acid, tartaric acid, malic acid, benzoic acid, salicylic acid, phthalic acid, oleic acid, stearic acid and mixtures thereof. In an alternative embodiment, the etheramines of the invention may, in protonated form, have a surfactant as a counter ion, as obtained from e.g. linear alkyl benzene sulphonic acid.

Tertiary dialkyl-substituted polyether amines can be prepared from the respective primary polyether amines by reductive amination. Typical procedures involve the use of formaldehyde or other alkylaldehydes like ethanal, 1-propanal or 1-butanal in the presence of a hydrogen donor such as formic acid or the in the presence of hydrogen gas and a transition metal containing catalyst.

Alternatively, dialky-substituted tertiary polyether amines can be obtained by reacting a polyether alcohol with a dialkylamine like e.g. dimethylamine in the presence of a suitable transition metal catalyst, preferably in the additional presence of hydrogen and under continuous removal of the reaction water.

Applications:

The inventive etheramines and the inventive compositions comprising these etheramines may be used in personal care, especially in shampoo and body wash formulations.

They may also be used as curing agent for epoxy resins or as a reactant in the production of polymers but also in polyurethanes, polyureas, epoxy resins, polyamides or as thermoplastic polyamide adhesives.

The inventive etheramines have proved to be effective for removal of stains, particularly grease, from soiled material. Besides, cleaning compositions with inventive etheramines also do not have the cleaning negatives seen with conventional, amine cleaning compositions for hydrophilic bleachable stains, such as coffee, tea, wine, or particulates. Additionally, for stain removal from white fabric, cleaning compositions with inventive etheramines do not cause the whiteness negatives that commercially available, amine cleaning compositions cause.

A further advantage of cleaning compositions comprising the inventive etheramines is their ability to remove grease stains in cold water cleaning solutions, via pretreatment of the grease stain outside the washing machine, followed by cold water washing. Without being limited by theory, cold water solutions have the effect of causing greases to harden or solidify, making greases more resistant to removal, especially from fabric. Cleaning compositions with etheramines according to the present invention thereof however, are surprisingly effective when used in pretreatment followed by cold water cleaning.

As used herein the phrase "cleaning composition" includes compositions and formulations designed for cleaning soiled material. Such compositions include but are not limited to, laundry cleaning compositions and detergents, fabric softening compositions, fabric enhancing compositions, fabric freshening compositions, laundry prewash, laundry pretreat, laundry additives, spray products, dry cleaning agent or composition, laundry rinse additive, wash additive, post-rinse fabric treatment, ironing aid, unit dose formulation, delayed delivery formulation, liquid hand dishwashing composition, detergent contained on or in a porous substrate or nonwoven sheet, automatic dish-washing agent, hard surface cleaner, and other suitable forms that may be apparent to one skilled in the art in view of the teachings herein. Such compositions may be used as a pre-laundering treatment, a post-laundering treatment, may be added during the rinse or wash cycle of the laundering operation, or used in homecare cleaning applications. The cleaning compositions may have a form selected from liquid, powder, single-phase or multiphase unit dose, pouch, tablet, gel, paste, bar, or flake.

The cleaning compositions described herein may include from about 0.1% to about 10%, in some examples, from about 0.2% to about 5%, and in other examples, from about 0.5% to about 3%, by weight the composition, of an etheramine according to the present invention.

Surfactant System

The cleaning compositions comprise a surfactant system in an amount sufficient to provide desired cleaning properties. In some embodiments, the cleaning composition comprises, by weight of the composition, from about 1% to about 70% of a surfactant system. In other embodiments, the liquid cleaning composition comprises, by weight of the composition, from about 2% to about 60% of the surfactant system. In further embodiments, the cleaning composition comprises, by weight of the composition, from about 5% to about 30% of the surfactant system. The surfactant system may comprise a detersive surfactant selected from anionic surfactants, nonionic surfactants, cationic surfactants, zwitteronic surfactants, amphoteric surfactants, ampholytic surfactants, and mixtures thereof. Those of ordinary skill in the art will understand that a detersive surfactant encompasses any surfactant or mixture of surfactants that provide cleaning, stain removing, or laundering benefit to soiled material.

Adjunct Cleaning Additives

The cleaning compositions of the present disclosure may also contain adjunct cleaning additives. Suitable adjunct cleaning additives include builders, structurants or thickeners, clay soil removal/anti-redeposition agents, polymeric soil release agents, polymeric dispersing agents, polymeric grease cleaning agents, enzymes, enzyme stabilizing systems, bleaching compounds, bleaching agents, bleach activators, bleach catalysts, brighteners, dyes, hueing agents, dye transfer inhibiting agents, chelating agents, suds supressors, softeners, and perfumes.

Methods of Use

The present disclosure includes methods for cleaning soiled material. As will be appreciated by one skilled in the art, the cleaning compositions of the present disclosure are suited for use in laundry pretreatment applications, laundry cleaning applications, and home care applications. Such methods include, but are not limited to, the steps of contacting cleaning compositions in neat form or diluted in wash liquor, with at least a portion of a soiled material and then optionally rinsing the soiled material. The soiled material may be subjected to a washing step prior to the optional rinsing step.

For use in laundry pretreatment applications, the method may include contacting the cleaning compositions described herein with soiled fabric. Following pretreatment, the soiled fabric may be laundered in a washing machine or otherwise rinsed.

Machine laundry methods may comprise treating soiled laundry with an aqueous wash solution in a washing machine having dissolved or dispensed therein an effective amount of a machine laundry cleaning composition in accord with the invention. An "effective amount" of the cleaning composition means from about 20 g to about 300 g of product dissolved or dispersed in a wash solution of volume from about 5 L to about 65 L. The water temperatures may range from about 5° C. to about 100° C. The water to soiled material (e.g., fabric) ratio may be from about 1:1 to about 20:1. In the context of a fabric laundry composition, usage levels may also vary depending not only on the type and severity of the soils and stains, but also on the wash water temperature, the volume of wash water, and the type of washing machine (e.g., top-loading, front-loading, top-loading, vertical-axis Japanese-type automatic washing machine).

The cleaning compositions herein may be used for laundering of fabrics at reduced wash temperatures. These methods of laundering fabric comprise the steps of delivering a laundry cleaning composition to water to form a wash liquor and adding a laundering fabric to said wash liquor, wherein the wash liquor has a temperature of above 0° C. to about 20° C., or to about 15° C., or to about 10° C. The fabric may be contacted to the water prior to, or after, or simultaneous with, contacting the laundry cleaning composition with water.

Another method includes contacting a nonwoven substrate impregnated with an embodiment of the cleaning composition with soiled material. As used herein, "nonwoven substrate" can comprise any conventionally fashioned nonwoven sheet or web having suitable basis weight, caliper (thickness), absorbency, and strength characteristics. Non-limiting examples of suitable commercially available non-woven substrates include those marketed under the trade-names SON-TARA® by DuPont and POLYWEB® by James River Corp.

Hand washing methods, and combined handwashing with semiautomatic washing machines, are also included.

Machine Dishwashing Methods

Methods for machine-dishwashing or hand dishwashing soiled dishes, tableware, silverware, or other kitchenware, are included. One method for machine dishwashing comprises treating soiled dishes, tableware, silverware, or other kitchenware with an aqueous liquid having dissolved or dispensed therein an effective amount of a machine dishwashing composition in accord with the present disclosure. By an effective amount of the machine dishwashing composition it is meant from about 8 g to about 60 g of product dissolved or dispersed in a wash solution of volume from about 3 L to about 10 L.

One method for hand dishwashing comprises dissolution of the cleaning composition into a receptacle containing water, followed by contacting soiled dishes, tableware, silverware, or other kitchenware with the dishwashing liquor, then hand scrubbing, wiping, or rinsing the soiled dishes, tableware, silverware, or other kitchenware. Another method for hand dishwashing comprises direct application of the cleaning composition onto soiled dishes, tableware, silverware, or other kitchenware, then hand scrubbing, wiping, or rinsing the soiled dishes, tableware, silverware, or other kitchenware. In some examples, an effective amount of cleaning composition for hand dishwashing is from about 0.5 mL to about 20 mL diluted in water.

Packaging for the Compositions

The cleaning compositions described herein can be packaged in any suitable container including those constructed from paper, cardboard, plastic materials, and any suitable laminates. An optional packaging type is described in European Application No. 94921505.7.

Multi-Compartment Pouch Additive

The cleaning compositions described herein may also be packaged as a multi-compartment cleaning composition.

The examples which follow illustrate the invention without imposing any limitation.

SYNTHESIS EXAMPLES

In the examples, the following abbreviations are used:

Example 1: 1 Mole 1,2-Propanediol+4 Mole Butylene Oxide, Aminated a) 1 Mole 1,2-Propandiol+4 Mole Butylene Oxide A 2 L autoclave was charged with 152.2 g 1,2-propanediol and 1.5 g potassium tert.-butylate and heated to 120° C. The autoclave was purged three times with nitrogen and heated to 140° C. 576.0 g butylene oxide was added in portions within 10 h. To complete the reaction, the mixture was stirred and allowed to post-react for additional 8 hours at 140° C. The reaction mixture was stripped with nitrogen and volatile compounds were removed in vacuo at 80° C. The catalyst was removed by adding 23.0 g synthetic magnesium silicate (Macrosorb MP5plus, Ineos Silicas Ltd.), stirring at 100° C. for 2 hours and filtration.

A light yellowish oil was obtained (730.1 g, hydroxy value: 251.7 mgKOH/g).

b) 1 Mole 1,2-Propanediol+4 Mole Butylene Oxide, Aminated

In a 9 L autoclave 650 g of the resulting liquid diol mixture from example 1-a, 1050 mL THF and 1500 g ammonia were mixed in presence of 200 mL of a solid catalyst as described in EP 0 696 572 B1. The catalyst containing nickel, copper, molybdenum and zirconium was in the form of 3×3 mm tablets. The autoclave was purged with hydrogen and the reaction was started by heating the autoclave. The reaction mixture was stirred for 15 hours at 205° C., the total pressure was maintained at 280 bar by purging hydrogen during the entire reductive amination step. After cooling down the autoclave the final product was collected, filtered, vented of excess ammonia and stripped on a rotary evaporator to remove light amines and water. A total of 500 grams of a low-color etheramine mixture was recovered. The analytical results thereof are shown in Table 1.

TABLE 1

Analytical results of the etheramine of Example 1

| Total amine-value mg KOH/g | Total acetylatables mg KOH/g | Secondary and tertiary amine value mg KOH/g | Tertiary amine-value mg KOH/g | Hydroxyl value mg KOH/g | Grade of amination in % | Primary Amine in % of total amine |
|---|---|---|---|---|---|---|
| 294.00 | 301.30 | 0.46 | 0.19 | 7.49 | 97.52 | 99.84 |

Comparative Example 1

Polyetheramine (2-Aminomethylethyl)-omega-(2-aminomethylethoxy)poly(oxy(methyl-1,2-ethandlyl)), sold under the trade name Polyetheramine D 230 or JEFFAMINE® D-230 by Huntsman, Tex., United States of America.

Comparative Example 2

1,2-Bis(2-aminoethoxy)ethane 97%, CAS-NR: 929-59-9, purchased from ABCR GmbH, Germany.

Comparative Example 3

Ethylene glycol bis(2-aminopropyl)ether 98%, CAS-NR: 2997-01-5, purchased from ABCR GmbH, Germany.

Use as Additives in Laundry Detergents

Stain removal from the swatches was calculated as follows:

$$\text{Stain Removal Index (SRI)} = (\Delta E_{initial} - \Delta E_{washed}) \cdot 100 / \Delta E_{initial}$$

$\Delta E_{initial}$=Stain level before washing
$\Delta E_{washed}$=Stain level after washing $\Delta E$ is calculated as CIE 1976 color difference according to DIN EN ISO 11664-4 (June 2012). $\Delta E_{initial}$ is calculated with L*, a*, b* values measured on fabric without stain and the L*, a*, b* values measured on the greasy stain before washing. $\Delta E_{washed}$ is calculated with L', a', b* values measured on fabric without stain and the L*, a*, b* values measured on the greasy stain after washing. Standard colorimetric measurement was used to obtain L', a* and b* values.

Application Example 1

Technical stain swatches of blue knitted cotton containing Beef Fat, Pork Fat and Bacon Grease were purchased from Warwick Equest Ltd. and washed in conventional western European washing machines (Miele Waschmaschine Softronic W 2241), selecting a 59 min washing cycle without heating (wash at 17° C.) and using 75 g of liquid detergent composition LA1 (see Table 2) together with or without 1.25 g of etheramine additive and some hydrochloric acid to readjust the pH after addition of the etheramine (pH of 75 g of LA1 in 1 L water should be at pH=8.3). Water hardness was 2.5 mM ($Ca^{2+}$:$Mg^{2+}$ was 3:1).

Six replicates for each stain type have been carried out. Given below are the averaged values. Stain level corresponds to the amount of grease on the fabric. The stain level of the fabric before the washing ($\Delta E_{initial}$) is high, in the washing process stains are diminished and the stain level after washing is smaller ($\Delta E_{washed}$). The better the stains have been removed the lower the value for $\Delta E_{washed}$ will be and the higher the difference will be to $\Delta E_{initial}$. Therefore the value of stain removal index increases with better washing performance.

TABLE 2 liquid detergent composition LA1

| Ingredients of liquid detergent composition LA1 | percentage by weight |
|---|---|
| Alkyl Benzene sulfonate[1] | 7.50% |
| AE3S[2] | 2.60% |
| AE9[3] | 0.40% |
| NI 45-7[4] | 4.40% |
| Citric Acid | 3.20% |
| C1218 Fatty acid | 3.10% |
| Amphiphilic polymer[5] | 0.50% |
| Zwitterionic dispersant[6] | 1.00% |
| Ethoxylated Polyethyleneimine[7] | 1.51% |
| Protease[8] | 0.89% |
| Natalase[9] | 0.21% |
| Chelant[10] | 0.28% |
| Brightener[11] | 0.09% |
| Solvent | 7.35% |
| Sodium Hydroxide | 3.70% |
| Fragrance & Dyes | 1.54% |
| Water, filler, stucturant | To Balance |

[1]Linear alkylbenenesulfonate having an average aliphatic carbon chain length C11-C12 supplied by Stepan, Northfield Illinois, USA
[2]AE3S is C12-15 alkyl ethoxy (3) sulfate supplied by Stepan, Northfield, Illinois, USA
[3]AE9 is C12-14 alcohol ethoxylate, with an average degree of ethoxylation of 9, supplied by Huntsman, Salt Lake City, Utah, USA
[4]NI 45-7 is C14-15 alcohol ethoxylate, with an average degree of ethoxylation of 7, supplied by Huntsman, Salt Lake City, Utah, USA
[5]Amphilic polymer is a polyvinyl acetate grafted polyethylene oxide copolymer having a poly-ethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.
[6]A compound having the following general structure: bis((C2H5O)(C2H4O)n)(CH3)—N+—CxH2x—N+—(CH3)-bis((C2H5O)(C2H4O)n), wherein n = from 20 to 30, and x = from 3 to 8, or sulphated or sulphonated variants thereof
[7]Polyethyleneimine (MW = 600) with 20 ethoxylate groups per —NH
[8]Protease may be supplied by Genencor International, Palo Alto, California, USA
[9]Natalase ® is a product of Novozymes, Bagsvaerd, Denmark.
[10]A suitable chelant is diethylene triamine penta(methyl phosphonic) acid supplied by Solutia, St Louis, Missouri, USA;
[11]Fluorescent Brightener 1 is Tinopal ® AMS, Fluorescent Brightener 2 supplied by Ciba Specialty Chemicals, Basel, Switzerland

TABLE 3

Wash results (given in SRI units)

| | Beef Fat | Pork Fat | Bacon Grease |
|---|---|---|---|
| Composition A | 70.2 | 70.1 | 69.2 |
| Composition B | 72.1 | 70.9 | 71.4 |
| Composition C | 78.3 | 76.3 | 80.0 |

Composition A: liquid detergent composition LA1 (see Table 2) without additional etheramine additive
Composition B: liquid detergent composition LA1 (see Table 2) with Comparative Example 1, polyetheramine (2-Aminomethylethyl)-omega-(2-aminomethylethoxy)-poly (oxy(methyl-1,2-ethandiyl)), sold under the trade name Polyetheramine D 230 or JEFFAMINE ® D-230
Composition C: liquid detergent composition LA1 (see Table 2) with 1,2-Propanediol + 4 butylene oxide, aminated, preparation of etheramine described in Example 1

The cleaning composition with the etheramine according to the invention (see Table 3: Composition C) shows superior grease cleaning effects over the detergent composition without etheramines (see Table 3: Composition A) and also shows superior grease cleaning effects over the cleaning composition with the etheramine of the Comparative Example 1 (see Table 3: B).

Application Example 2

In the following examples, the individual ingredients within the cleaning compositions are expressed as percentages by weight of the cleaning compositions.

Liquid Detergent A (see Table 4) is a conventional laundry detergent that uses the Comparative Example 1, Polyetheramine D 230; Liquid Detergent B (see Table 4) contains instead the etheramine described by Example 1.

Technical stain swatches of cotton CW120 containing burnt butter, hamburger grease, margarine, taco grease were purchased from Empirical Manufacturing Co., Inc (Cincinnati, Ohio). The swatches were washed in a Miele front loader washing machine, using 14 grains per gallon water hardness and washed at 15° C. The total amount of liquid detergent used in the test was 80 grams. Image analysis was used to compare each stain to an unstained fabric control. Software converted images taken into standard colorimetric values and compared these to standards based on the commonly used Macbeth Colour Rendition Chart, assigning each stain a colorimetric value (Stain Level). Eight replicates of each were prepared.

TABLE 4 composition of the liquid detergents

| | Liquid Detergent A (%) | Liquid Detergent B (%) |
|---|---|---|
| AES $C_{12-15}$ alkyl ethoxy (1.8) sulfate | 14.0 | 14.0 |
| Alkyl benzene sulfonic acid | 2.0 | 2.0 |
| Nonionic 24-9[4] | 1.0 | 1.0 |
| C12/14 Amine Oxide | 0.2 | 0.2 |
| Etheramine[2] | — | 1.0 |
| Polyetheramine[3] | 1.0 | — |
| Citric Acid | 3.4 | 3.4 |
| Borax | 2.8 | 2.8 |
| Zwitterionic dispersant[5] | 1.1 | 1.1 |
| Ethoxylated Polyethyleneimine[1] | 1.5 | 1.5 |
| Sodium hydroxide | 3.7 | 3.7 |
| DTPA[6] | 0.3 | 0.3 |
| Protease | 0.8 | 0.8 |
| Amylase: Natalase ® | 0.14 | 0.14 |
| 1,2-Propanediol | 3.9 | 3.9 |
| Monoethanolamine (MEA) | 0.3 | 0.3 |
| Sodium Cumene Sulfonate | 0.9 | 0.9 |
| Water & other components | Balance | Balance |
| pH | 8.3 | 8.3 |

[1]Polyethyleneimine (MW = 600) with 20 ethoxylate groups per —NH
[2]The etheramine composition as described in Example 1
[3]Polyetheramine (2-Aminomethylethyl)-omega-(2-aminomethylethoxy)-poly(oxy(methyl-1,2-ethandiyl)), sold under the trade name Polyetheramine D 230.
[4]Nonionic 24-9 is a C12-14 alcohol ethoxylate, with an average degree of ethoxylation of 9
[5]A compound having the following general structure: bis((C2H5O)(C2H4O)n)(CH3)—N+—CxH2x—N+—(CH3)-bis((C2H5O)(C2H4O)n), wherein n = from 20 to 30, and x = from 3 to 8, or sulphated or sulphonated variants thereof
[6]DTPA is diethylenetetraamine pentaacetic acid Stain removal index scores for each stain were calculated as described above and are listed in Table 5.

TABLE 5

Cleaning Results

| Soils | Liquid Detergent A | Liquid Detergent B (results given as delta SRI vs. Liquid Detergent A) |
|---|---|---|
| Margarine | 88.2 | 1.7 |
| Grease burnt butter | 76.7 | 5.1 |
| Grease hamburger | 68.0 | 8.2 |
| Grease taco | 55.2 | 7.4 |

These results illustrate the surprising grease removal benefit of the etheramine of Example 1 as compared to the Comparative Example 1, Polyetheramine D 230 especially on difficult-to-remove, high-frequency consumer stains like hamburger grease and taco grease.

Application Example 3

Technical stain swatches of blue knitted cotton containing Sausage Fat, Chicken Fat and Bacon Grease were purchased from Warwick Equest Ltd. and washed in conventional western European washing machines (Miele Waschmaschine Softronic W 2241), selecting a 59 min washing cycle without heating and using 75 g of liquid detergent composition LA1 (Table 2 of Application Example 1). To assess the performance of the polyetheramine additive there were added to the detergent composition 1.125 g of polyetheramine additive of Example 1 or 1.160 g of polyetheramine of Comparative Example 2 or 1.148 g of polyetheramine of Comparative Example 3 and some hydrochloric acid to re-adjust the pH after addition of the polyetheramine. (pH of 75 g of LA1 in 1 L water should be at pH=8.3.) Water hardness was 2.5 mM ($Ca^{2+}:Mg^{2+}$ was 3:1).

Four replicates for each stain type have been carried out. Given below are the averaged values. Stain level corresponds to the amount of grease on the fabric. The stain level of the fabric before the washing ($\Delta E_{initial}$) is high, in the washing process stains are removed and the stain level after washing is smaller ($\Delta E_{washed}$). The better the stains have been removed the lower the value for $\Delta E_{washed}$ will be and the higher the difference will be to $\Delta E_{initial}$. Therefore the value of stain removal index increases with better washing performance.

TABLE 6

Wash results (given in SRI units)

| | Sausage Fat | Chicken Fat | Bacon Grease |
|---|---|---|---|
| Composition D | 61.2 | 59.0 | 58.8 |
| Composition E | 69.2 | 67.7 | 68.0 |
| Composition F | 63.2 | 61.5 | 60.3 |
| Composition G | 63.2 | 62.3 | 62.2 |

Composition D: Liquid detergent composition LA1 (see Table 2) without additional etheramine additive
Composition E: Liquid detergent composition LA1 (see Table 2) with polyetheramine of Example 1
Composition F: Comparative example: Liquid detergent composition LA1 (see Table 2) with polyetheramine Comparative Example 2 (1,2-Bis(2-aminoethoxy)ethane)
Composition G: Comparative example: Liquid detergent composition LA1 (see Table 2) with polyetheramine Comparative Example 3 (Ethylene glycol bis(2-aminopropyl)ether)

The cleaning composition with the etheramine according to the invention (see Table 6: Composition E) shows superior grease cleaning effects over the detergent composition without etheramines (see Table 6: Composition D) and also shows superior grease cleaning effects over the cleaning composition with the etheramine of the Comparative Example 2 and 3 (see Table 6: Composition F and G).

The invention claimed is:
1. A mixture of etheramines of formula (I)

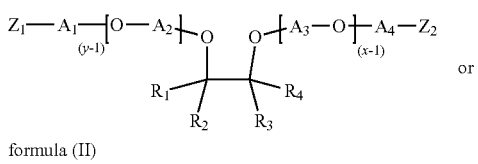

or formula (II)

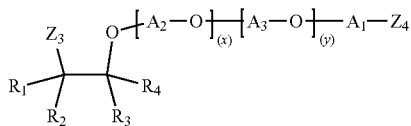

wherein $R_1$, $R_2$, $R_3$ and $R_4$ are independently selected from the group consisting of H, a methyl group and an ethyl group;
$A_1$, $A_2$, $A_3$ and $A_4$ are independently selected from the group consisting of linear alkylenes having 2 to 18 carbon atoms and branched alkylenes having 2 to 18 carbon atoms;
wherein at least three selected from the group consisting of $A_1$, $A_2$, $A_3$ and $A_4$ are linear or branched butylene;
the sum of x+y is in the range of 3 to 100 and x≥1 and y≥1;
$Z_1$-$Z_4$ are independently selected from OH, $NH_2$, NHR' or NR'R", wherein at least one of $Z_1$-$Z_2$ and at least one of $Z_3$-$Z_4$ is $NH_2$, NHR' or NR'R", wherein R' and R" are independently selected from alkylenes having 2 to 6 carbon atoms.

2. The mixture according to claim 1, wherein x+y is in the range of from 3 to 10.

3. The mixture according to claim 1, wherein $A_1$, $A_2$, $A_3$ and $A_4$ are linear or branched butylene.

4. The mixture according to claim 1, wherein $R_1$ is a methyl group and $R_2$, $R_3$ and $R_4$ are H.

5. The mixture according to claim 1, wherein $Z_1$-$Z_4$ are $NH_2$.

6. The mixture according to claim 1, wherein said etheramine of formula (I) or formula (II) has a weight average molecular weight of about 250 to about 700 grams/mole.

7. A composition comprising the mixture as defined in claim 1 and further comprises an etheramine of formula (VI)

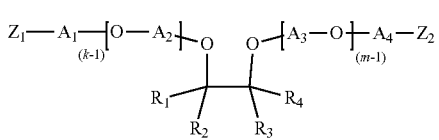

and/or an etheramine of formula (VII)

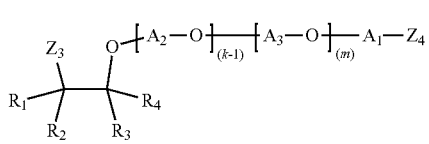

wherein $R_1$, $R_2$, $R_3$ and $R_4$ are independently selected from the group consisting of H, a methyl group and an ethyl group;
$A_1$, $A_2$, $A_3$ and $A_4$ are independently selected from the group consisting of linear alkylenes having 2 to 18 carbon atoms and branched alkylenes having 2 to 18 carbon atoms;
wherein at least one of $A_1$, $A_2$, $A_3$ and $A_4$ is linear or branched butylene;
the sum of k+m is below 3 and wherein k≥1 and m≥1;
$Z_1$-$Z_4$ are independently selected from OH, $NH_2$, NHR' or NR'R", wherein at least one of $Z_1$-$Z_2$ and at least one of $Z_3$-$Z_4$ is $NH_2$, NHR' or NR'R", wherein R' and R" are independently selected from alkylenes having 2 to 6 carbon atoms.

8. The mixture according to claim 1, wherein the etheramine mixture is reacted with an acid.

9. A process for the manufacture of the mixture as defined in claim 1 comprising the following steps:
a) reacting a dialcohol of Formula (III) with $C_2$-$C_{18}$ alkylene oxides, wherein the molar ratio of dialcohol to $C_2$-$C_{18}$ alkylene oxides is in the range of from 1:3 to 1:10,

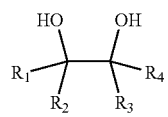

wherein $R_1$, $R_2$, $R_3$ and $R_4$ are independently selected from the group consisting of H, a methyl group or an ethyl group; and
b) aminating the alkoxylated dialcohols with ammonia.

10. The process according to claim 9, wherein the molar ratio of dialcohol to $C_2$-$C_{18}$ alkylene oxides is in the range of 1:3 to 1:4.

11. The process according to claim 9, wherein the $C_2$-$C_{18}$ alkylene oxides are selected from the group consisting of ethylene oxide, propylene oxide, butylene oxide or a mixture thereof.

12. The process according to claim 9, wherein the $C_2$-$C_{18}$ alkylene oxide is butylene oxide.

13. The process according to claim 9, wherein the dialcohol of formula (III) is selected from the group consisting of 1,2-propanediol, 1,2-butanediol, 1,2-ethanediol, 3,4-hexanediol and 2,3-pentanediol.

14. The process according to claim 9, wherein the amination is carried out in the presence of copper-containing catalyst, nickel-containing catalyst or cobalt-containing catalyst.

15. A personal care composition comprising the mixture as defined in claim 1.

16. A shampoo and/or body wash formulation comprising the mixture as defined in claim 1.

17. A curing agent for epoxy resins or as a reactant in the production of polymers comprising the mixture as defined in claim 1.

18. A polyurethane, polyurea, or a thermoplastic polyamide adhesives comprising the mixture as defined in claim 1.

19. The mixture according to claim 3, wherein $R_1$ is a methyl group and $R_2$, $R_3$ and $R_4$ are H and $Z_1$-$Z_4$ are $NH_2$.

* * * * *